(12) United States Patent
Johnsen

(10) Patent No.: US 7,555,103 B2
(45) Date of Patent: *Jun. 30, 2009

(54) MULTI-LEAF COLLIMATOR WITH LEAVES FORMED OF DIFFERENT MATERIALS

(75) Inventor: Stanley Woodrow Johnsen, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/168,757

(22) Filed: Jul. 7, 2008

(65) Prior Publication Data

US 2008/0267356 A1 Oct. 30, 2008

Related U.S. Application Data

(63) Continuation of application No. 11/712,640, filed on Feb. 28, 2007, now Pat. No. 7,397,901.

(51) Int. Cl.
G21K 1/04 (2006.01)
G21K 1/02 (2006.01)
(52) U.S. Cl. ...................................... 378/152; 378/147
(58) Field of Classification Search ......... 378/145–153; 250/505.1
See application file for complete search history.

(56) References Cited

U.S. PATENT DOCUMENTS

| 6,822,252 | B2 * | 11/2004 | Svatos et al. ............. 250/505.1 |
| 2003/0031298 | A1 * | 2/2003 | Xing .......................... 378/147 |
| 2007/0127624 | A1 * | 6/2007 | Seeber et al. ............... 378/147 |

* cited by examiner

*Primary Examiner*—Irakli Kiknadze

(57) ABSTRACT

A multi-leaf collimator includes a number of independently adjustable leaves. Adjacent leaves overlap to prevent an incident beam of radiation from passing through a gap between them. The overlapping portions of the leaves are made of a first material, while the non-overlapping portions of the leaves are made of a second, different material.

25 Claims, 5 Drawing Sheets

MULTI-LEAF COLLIMATOR WITH LEAVES FORMED OF DIFFERENT MATERIALS

RELATED UNITED STATES PATENT APPLICATION

This application is a Continuation Application of the commonly-owned U.S. patent application with Ser. No. 11/712,640, now U.S. Pat. No. 7,397,901, filed Feb. 28, 2007, by S. Johnsen, and entitled "A Multi-Leaf Collimator with Leaves Formed of Different Materials."

TECHNICAL FIELD

Embodiments of the invention relate generally to radiation shielding. More specifically, embodiments of the invention pertain to a multi-leaf collimator that can be used in applications such as radiotherapy.

BACKGROUND

Multi-leaf collimators (MLC) are commonly used in radiotherapy machines. Typically, an MLC includes two sets of independently adjustable leaves. Each leaf is thick enough to attenuate or block completely a beam of radiation. The first set of leaves is positioned on one side of the beam's path, and the second set mirrors the first set on the other side of the beam's path. The leaves can be positioned independently of one another to form an aperture in a shape like that of the area to be irradiated, so that only the targeted area is irradiated while surrounding areas are shielded.

Because adjacent leaves need to be able to move relative to one another, there is necessarily a gap between them. The leaves are designed so that one or more portions of one leaf overlap one or more corresponding portions of an adjacent leaf. Thus, the gap between adjacent leaves does not provide a straight-line passageway for the radiation beam. Instead, radiation that enters a gap will encounter a thickness of leaf material that is sufficient for attenuating or blocking the radiation. In this manner, leakage of radiation through the gaps to areas other than the targeted area is prevented.

SUMMARY

Conventional MLC leaves may be formed using only a high density material or a material with a high atomic number (referred to as a high-Z material). High density/high-Z material is more effective at blocking a radiation beam than low density/low-Z material. However, for proton beams, the use of high density/high-Z material in an MLC can result in the production of more neutrons than the use of low density/low-Z material. Additional neutrons can be undesirable because they contribute to the total dose received by a patient. High density/high-Z material can also be difficult to machine and relatively expensive, and leaves made from such material are heavier and hence more difficult to move than leaves made of low density/low-Z material. On the other hand, conventional leaves made only of low density/low-Z material are thicker—perhaps substantially thicker—than leaves made of high density/high-Z material.

According to an embodiment of the present invention, an MLC includes a number of independently adjustable and overlapping leaves. The overlapping portions of the leaves are made of a first material, while the non-overlapping portions of the leaves are made of a second, different material. The first material is denser (or has a higher atomic number) than the second material. Accordingly, the majority of each leaf is made using the second (e.g., less dense) material, while a smaller portion of each leaf is made from the first (e.g., denser) material. Consequently, leaves made using a combination of low density (or low-Z) and high density (or high-Z) materials can be lighter, less expensive, easier to fabricate and will produce less neutrons than conventional leaves made using only a high density or high-Z material, and thinner than conventional leaves made using only a low density or low-Z material.

BRIEF DESCRIPTION OF THE DRAWINGS

The accompanying drawings, which are incorporated in and form a part of this specification, illustrate embodiments of the invention and, together with the description, serve to explain the principles of the invention.

Unless noted otherwise, the drawings are not to scale.

DETAILED DESCRIPTION

Reference will now be made in detail to embodiments of the present invention. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims.

Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, and components have not been described in detail as not to unnecessarily obscure aspects of the present invention.

Figure 1:
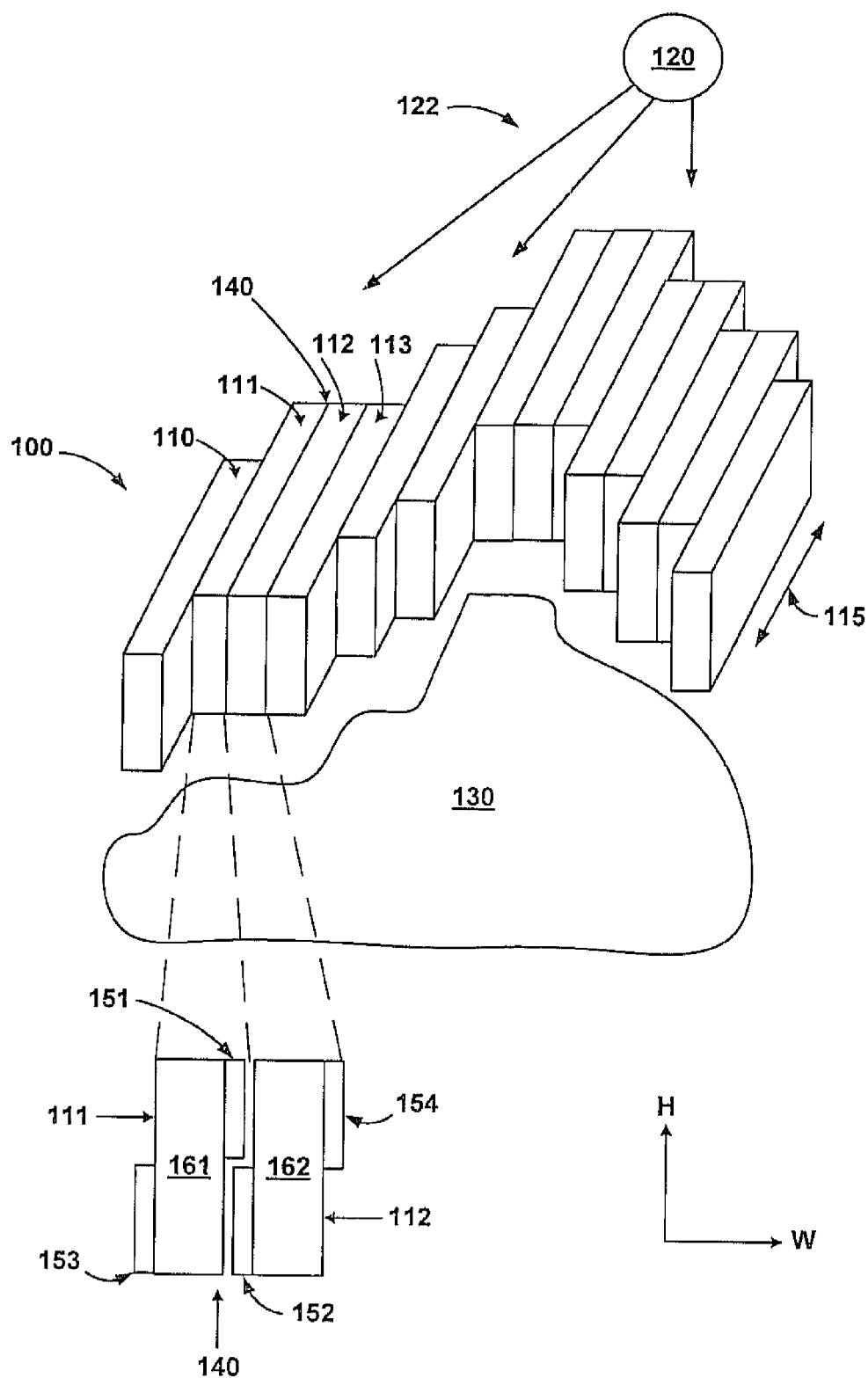
FIG. 1 is a perspective view of a portion of a multi-leaf collimator (MLC), including a cross-sectional view of adjacent leaves, in accordance with one embodiment of the present invention.

FIG. 1 is a perspective view of a portion of a multi-leaf collimator (MLC) 100 in accordance with one embodiment of the present invention. Generally speaking, MLC 100 is designed to define and restrict (constrict) the dimensions of a radiation beam 122. In one embodiment, MLC 100 is implemented as part of a radiotherapy machine. In one embodiment, radiation beam 122 is a beam of x-rays, and in another embodiment, radiation beam 122 is a beam of charged particles such as protons, electrons or heavy ions.

Figure 2:
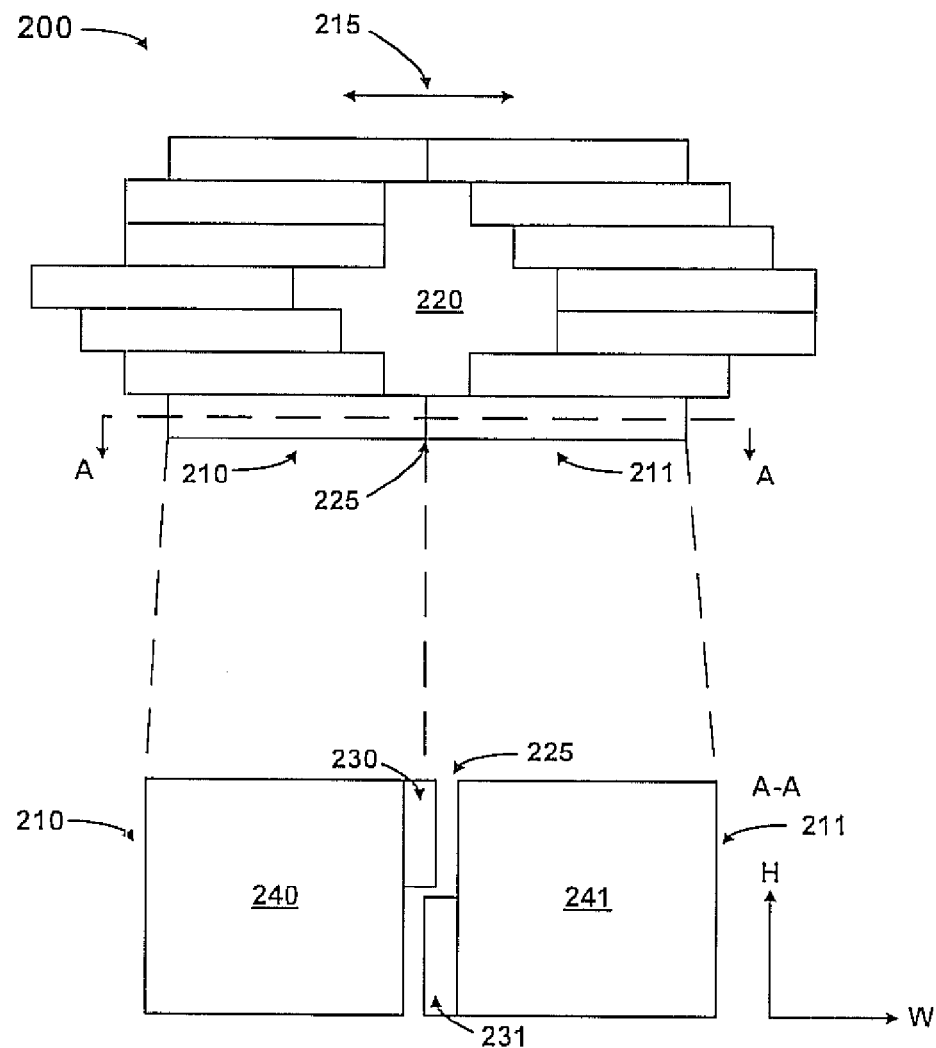
FIG. 2 is a top-down view of a portion of an MLC, including a cross-sectional view of adjacent leaves, in accordance with one embodiment of the present invention.

In the example of FIG. 1, MLC 100 includes a set of plates or leaves, exemplified by leaves 110, 111, 112 and 113. Leaves 111 and 112 are also isolated in cross-sectional view. MLC 100 may include other components not illustrated or discussed herein, such as guides or tracks for the leaves, drive mechanisms, suspension mechanisms, and so on. As illustrated in FIG. 2, there may be a second set of leaves opposing the first set in a symmetrical or mirror-like fashion. In the examples of FIGS. 1 and 2, any leaf can be adjusted independently of any other leaf. There is a gap (e.g., gap 140) between adjacent leaves (e.g., leaves 111 and 112) so that the leaves can move relative to one another. Leaves can be moved back and forth in the directions indicated by the arrows 115 and 215.

With reference to FIG. 1, the MLC 100 is situated between a source 120 of the radiation beam 122 and a target area 130. The shape of the target area 130—that is, the shape of the area to be exposed to the beam 122—is defined by positioning the leaves of the MLC 100 accordingly. The leaves block portions of the beam 122, while other portions of the beam reach the defined target area 130 unblocked. Unless otherwise indicated, the word "block" is used herein in the general sense to mean either "prevent" (completely block) or "hinder" (partially block or attenuate). Thus, areas outside of the target area 130 are shielded at least to some extent from the beam 122, so that areas outside the target area are not exposed to unnecessary levels of radiation.

The leaves 111 and 112 are designed with overlapping portions 151 and 152, respectively, which are situated between adjacent surfaces of those leaves. In the discussion herein, an overlapping portion 151 or 152 of a leaf may be referred to as the "first portion" of a leaf, while the portion of a leaf other than the overlapping portion (e.g., portion 161 or 162) may be referred to as the "second portion" or the "non-overlapping portion" of the leaf. The overlapping portions 151 and 152 can also be described as being complementary. In the example of FIG. 1, leaf 111 also includes an overlapping portion 153 that is situated between adjacent surfaces of leaf 111 and adjacent leaf 110, and leaf 112 also includes an overlapping portion 154 that is situated between leaf 112 and an adjacent leaf 113. Each leaf in MLC 100 may be similarly designed.

The portions 161 and 162 each have a width (measured in the direction W of FIG. 1) and a height or thickness (measured in the direction H of FIG. 1). In a radiotherapy machine that uses x-rays, for example, the x-rays will be attenuated as they pass through a portion 161 or 162, in which case the portions 161 and 162 can each be made thick enough to reduce the x-ray dosage by a desired amount. In contrast to x-rays, charged particles such as protons and heavy ions are not attenuated in number but have a definite range in a given material. Accordingly, in a radiotherapy machine that uses charged particles, the portions 161 and 162 can each be made thick enough to completely block the charged particles. That is, the thickness of material used to form each of the portions 161 and 162 meets or exceeds the range of charged particles in the material.

Also, in a radiotherapy machine that uses x-rays, the overlapping portions 151-154 can each be made thick enough to reduce the x-ray dosage by the desired amount. That is, overlapping portion 151 can by itself attenuate an x-ray by the desired amount, and overlapping portion 152 can also by itself attenuate an x-ray that enters gap 140 (bypassing overlapping portion 151) by the desired amount. Similarly, in a radiotherapy machine that uses charged particles, the overlapping portions 151-154 can each be made thick enough to completely block the charged particles. Thus, overlapping portion 151 can by itself completely block charged particles, and overlapping portion 152 can also by itself completely block charged particles that enter gap 140 (bypassing overlapping portion 151).

According to embodiments of the present invention, the overlapping portions 151-154 are made of a material that is different from the material used to make portions 161 and 162. In one embodiment, the overlapping portions 151-154 are made of a material (which may be referred to herein as the "first material") that has a higher density than the material (which may be referred to herein as the "second material") that makes up portions 161 and 162. In another embodiment, the overlapping portions 151-154 are made of a material that has a higher atomic number (a higher-Z material) than the material (a lower-Z material) that makes up portions 161 and 162. Higher density or higher-Z materials ("higher density/higher-Z materials") include, but are not limited to, tungsten, tungsten alloys, tantalum, tantalum alloys, lead or lead alloys, while lower density or lower-Z materials ("lower density/lower-Z materials") include, but are not limited to, steel (various steel alloys), brass, zinc or copper. Generally speaking, a higher density/higher-Z material may be a material that has a density of about 15 gm/cm$^3$ or greater.

In one embodiment, the width of an overlapping portion (e.g., portion 151) is approximately 0.25-0.5 mm, while the width of a non-overlapping portion is approximately 0.5-1 cm. In one embodiment, the height of an overlapping portion is approximately 3 cm while the height of a non-overlapping portion is approximately 6 cm.

In general, for each leaf of MLC 100, the volume of the non-overlapping portion is greater than the total volume of the overlapping portions. Thus, according to embodiments of the present invention, the bulk of each leaf in MLC 100 is made using a lower density/lower-Z material, while a lesser portion of each leaf is made using a higher density/higher-Z material. Leaves formed of different materials in this manner provide a number of advantages compared to leaves formed only of either higher density/higher-Z material or lower density/lower-Z material.

For one, because the leaves of MLC 100 utilize a reduced amount of higher density/higher-Z material relative to conventional leaves formed only of higher density/higher-Z material, they will weigh less than conventional leaves. Because they are lighter, the leaves of MLC 100 are easier to move and so the mechanisms for positioning them can be less robust. Also, higher density/higher-Z material can be difficult to work with (e.g., machine), and so by reducing the amount of such material, the leaves of MLC 100 can be easier to fabricate than conventional leaves. In addition, higher density/higher-Z material can be more expensive, and so by reducing the amount of such material, the leaves of MLC 100 can cost less than conventional leaves. Furthermore, higher density/higher-Z material produces more neutrons when subject to a proton beam or x-ray beam, and so by reducing the amount of such material, the neutron dose to a patient, for example, can be reduced.

On the other hand, because the leaves of MLC 100 still utilize higher density/higher-Z material in the overlapping portions of the leaves, the leaves of MLC 100 can be made thinner than conventional leaves formed only of lower density/lower-Z material. For example, the range of 250 MeV protons in brass is about 65 mm while their range in tungsten is about 40 mm. Because each of the overlapping portions 151-154 is thick enough by itself to block radiation beam 122, at a minimum the thicknesses of the portions 151-154 are equal. Therefore, at a minimum the thicknesses of the leaf portions 161 and 162 are each about twice the height of a single overlapping portion 151, 152, 153 or 154. Thus, in conventional leaves made only of brass, the minimum thickness of an overlapping portion 151-154 would be about 65 mm and the minimum thickness of a non-overlapping portion 161-162 would be about 130 mm. However, according to embodiments of the present invention, the overlapping portions (e.g., portions 151 and 153) of a leaf (e.g., leaf 111) may be made of tungsten, while the remaining portion (e.g., portion 161) of the leaf may be made of brass. If the thicknesses of the overlapping portions made of tungsten are to exceed the range of protons in tungsten, the minimum thickness of an overlapping portion 151-154 would be about 40 mm. Accordingly, the minimum thickness of a non-overlapping portion 161-162 would be about 80 mm, representing a significant reduction in the thickness of MLC 100 relative to a conventional MLC.

In general, fabrication of the leaves in MLC 100 (e.g., leaves 111 and 112) entails attaching or bonding the higher density/higher-Z portion and the lower density/lower-Z portion. This can be achieved in a number of different ways, depending on the materials used. The portions may be joined using a technique such as brazing, for example. Alternatively, the portions may be joined mechanically (e.g., using screws or other types of fasteners).

FIG. 2 is a top-down view of a portion of an MLC 200 in accordance with one embodiment of the present invention. MLC 200 includes a number of leaves exemplified by leaves 210 and 211, which are also shown in cross-section along axis A-A. The leaves can be independently moved back and forth in the direction of arrow 215, in order to create an aperture 220 that defines the shape of a targeted area. Generally speaking, the leaves 210 and 211 lie on a common axis and move back and forth along that axis. There is a gap 225 between opposing leaves (e.g. leaves 210 and 211) when those leaves are in the closed position.

Continuing with reference to FIG. 2, the leaves 210 and 211 are designed with overlapping portions 230 and 231, respectively, which are situated between adjacent surfaces of those leaves. Each leaf in MLC 200 may be similarly designed. As before, an overlapping portion 230 or 231 may be referred to as the "first portion" of a leaf, while the portion of a leaf other than the overlapping portion (e.g., portion 240 or 241) may be referred to as the "second portion" or "non-overlapping portion" of the leaf. The overlapping portions 230 and 231 can also be described as complementary.

The non-overlapping portions 240 and 241 each have a height or thickness (measured in the direction H of FIG. 2). In a radiotherapy machine that uses x-rays, for example, the x-rays will be attenuated as they pass through a portion 240 or 241, in which case the portions 240 and 241 can each be made thick enough to reduce the x-ray dosage by a desired amount. In a radiotherapy machine that uses charged particles, the portions 240 and 241 can each be made thick enough to completely block the charged particles. That is, the thickness of each of the portions 240 and 241 can be chosen to meet or exceed the range of the charged particles in the material used to form those portions.

Also, in a radiotherapy machine that uses x-rays, the overlapping portions 230 and 231 can each be made thick enough to reduce the x-ray dosage by the desired amount. That is, overlapping portion 230 can by itself attenuate an x-ray by the desired amount, and overlapping portion 231 can also by itself attenuate an x-ray that enters gap 225 (bypassing overlapping portion 230) by the desired amount. Similarly, in a radiotherapy machine that uses charged particles, the overlapping portions 230 and 231 can each be made thick enough to completely block the charged particles. Thus, overlapping portion 230 can by itself completely block charged particles, and overlapping portion 231 can also by itself completely block charged particles that enter gap 225 (bypassing overlapping portion 230).

According to embodiments of the present invention, the overlapping portions 230 and 231 are made of a material that is different from the material used to make non-overlapping portions 240 and 241. In one embodiment, the overlapping portions 230 and 231 are made of a material (which may be referred to herein as the "first material") that has a higher density than the material (which may be referred to herein as the "second material") that makes up portions 240 and 241. In another embodiment, the overlapping portions 230 and 231 are made of a higher-Z material than the material that makes up portions 240 and 241.

Thus, according to embodiments of the present invention, the bulk of each leaf in MLC 200 (that is, the second or non-overlapping portion of each leaf) is made from a less dense/lower-Z material than the overlapping (first) portions of each leaf. Leaves formed of different materials in this manner provide a number of advantages compared to leaves formed entirely of either higher density/higher-Z material or lower density/lower-Z material. Those advantages have been previously discussed herein.

Furthermore, the embodiments discussed in conjunction with FIG. 1 and the embodiments discussed in conjunction with FIG. 2 can be combined. That is, overlapping portions can be situated on adjacent surfaces of parallel leaves and on adjacent ends of opposing leaves.

Figure 3:
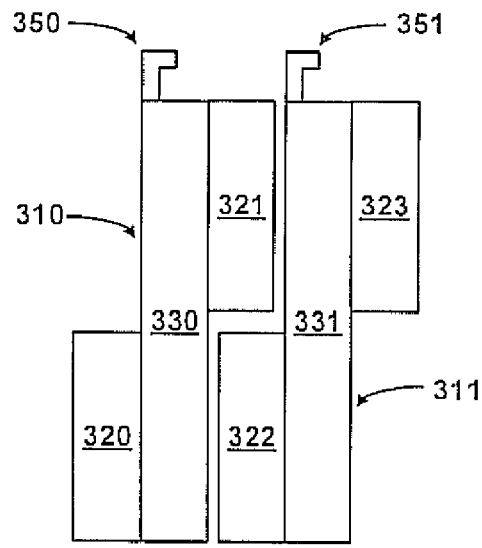
FIGS. 3, 4, 5 and 6 are cross-sectional views of adjacent leaves according to embodiments of the present invention.

FIG. 3 is a cross-sectional view of adjacent leaves 310 and 311 according to an embodiment of the present invention. Leaf 310 includes overlapping portions 320 and 321 and non-overlapping portion 330, and leaf 311 includes overlapping portions 322 and 323 and non-overlapping portion 331. The overlapping portions 320-323 are made of a material that is different from the material used to make portions 330 and 331. In one embodiment, the overlapping portions 320-323 are made of a material that has a higher density than the material that makes up portions 330 and 331. In another embodiment, the overlapping portions 320-323 are made of a higher-Z material than the material that makes up portions 330 and 331.

In the example of FIG. 3, the leaves 310 and 311 include structural elements 350 and 351, which represent features of the leaves such as drive mechanisms or suspension mechanisms. In one embodiment, the structural elements 350 and 351 are made of the same lower density/lower-Z material as the leaf portions 350 and 351. In one such embodiment, the structural elements 350 and 351 are machined from the same block of material used to form the leaf portions 330 and 331. As mentioned above, lower density/lower-Z material is easier to work with than higher density/higher-Z material. Thus, another advantage associated with forming the non-overlapping leaf portions from lower density/lower-Z material is that the structural elements 350 and 351 can be easier to machine. Leaf elements 320-323 may rely on the other parts of the leaves, such as elements 330 and 331, to provide structural strength. Therefore, the elements 320-323 may be made from material with lesser strength, such as lead or its alloys, than the material that makes up the other portions of the leaves. This provides more flexibility in the design of the leaves.

Figure 4:
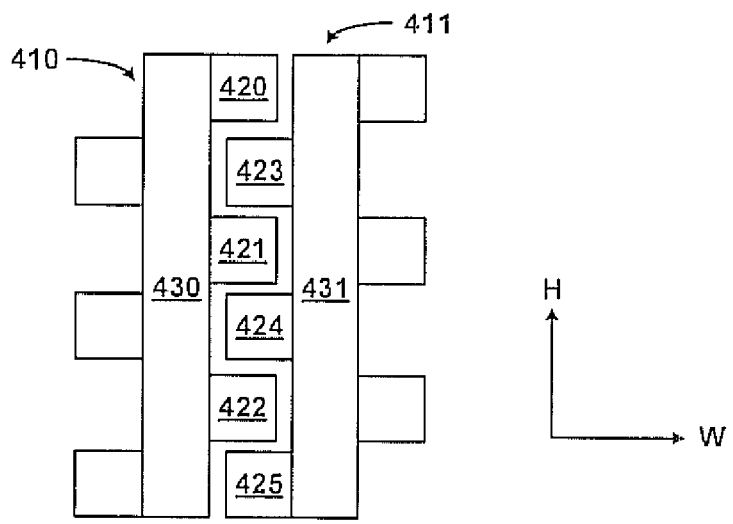
Figure 5:
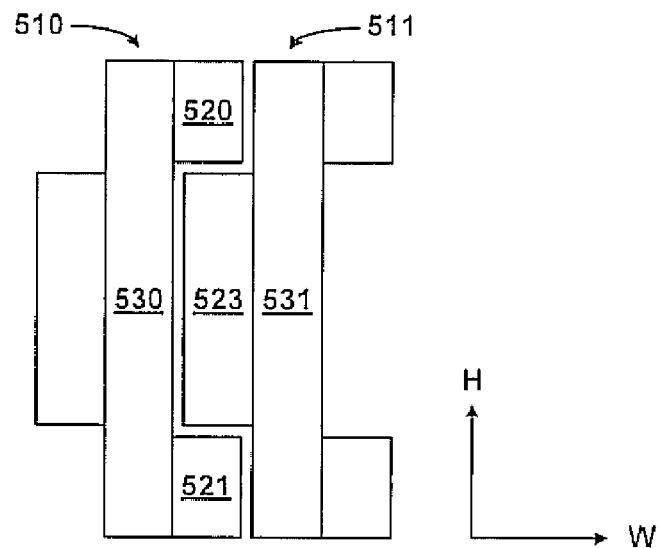

FIGS. 4 and 5 illustrate cross-sectional views of adjacent leaves according to other embodiments of the present invention. In the example of FIG. 4, adjacent leaves 410 and 411 are shown. Leaf 410 includes non-overlapping portion 430 and overlapping portions 420, 421 and 422 on the surface adjacent to leaf 411, and leaf 411 includes non-overlapping portion 431 and overlapping portions 423, 424 and 425 on the surface adjacent to leaf 410. The overlapping portions 420-422 may be collectively referred to as the "first portion" of leaf 410 and the overlapping portions 423-425 may be collectively referred to as the "first portion" of leaf 411. The overlapping portions 420-425 are made of a material that is different from the material used to make portions 430 and 431. In one embodiment, the overlapping portions 420-425 are made of a material that has a higher density than the material that makes up portions 430 and 431. In another embodiment, the overlapping portions 420-425 are made of a higher-Z material than the material that makes up portions 430 and 431. In general, the total thicknesses (H) of the overlapping portions 420-422, and of the overlapping portions 423-425, are sufficient to attenuate or completely block a radiation beam.

In the example of FIG. 5, adjacent leaves 510 and 511 are shown. Leaf 510 includes non-overlapping portion 530 and overlapping portions 520 and 521 on the surface adjacent to leaf 511, and leaf 511 includes non-overlapping portion 531 and overlapping portion 523 on the surface adjacent to leaf 510. The overlapping portions 520 and 521 may be collectively referred to as the "first portion" of leaf 510. The overlapping portions 520, 521 and 523 are made of a material that is different from the material used to make portions 530 and 531. In one embodiment, the overlapping portions 520, 521 and 523 are made of a material that has a higher density than the material that makes up portions 530 and 531. In another embodiment, the overlapping portions 520, 521 and 523 are made of a higher-Z material than the material that makes up portions 530 and 531. In general, the total thicknesses (H) of the overlapping portions 520 and 521, and of the overlapping portion 523, are sufficient to attenuate or completely block a radiation beam.

Figure 6:
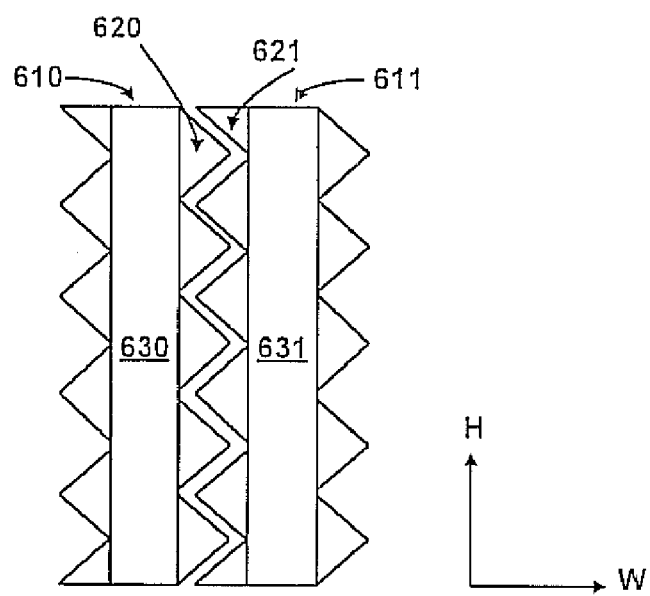

FIG. 6 illustrates a cross-sectional view of adjacent leaves 610 and 611 according to another embodiment of the present invention, referred to herein as a sawtooth embodiment. Leaf 610 includes non-overlapping portion 630 and a number of overlapping portions exemplified by portion 620, and leaf 611 includes non-overlapping portion 631 and a number of overlapping portions exemplified by portion 621. The overlapping portions 620 and 621 are made of a material that is different from the material used to make portions 630 and 631. In one embodiment, the overlapping portions 620 and 621 are made of a material that has a higher density than the material that makes up portions 630 and 631. In another embodiment, the overlapping portions 620 and 621 are made of a higher-Z material than the material that makes up portions 630 and 631.

The thickness (H) of each leaf 610 and 611 in the sawtooth embodiment depends on how closely the overlapping portions of adjacent leaves interleave. The thickness of each sawtooth (e.g., portion 620 or 621) changes with its width (W). If the overlapping portions are far enough apart, an x-ray or charged particle may encounter only the thinner portions of each sawtooth. Accordingly, leaf thickness will increase in proportion to the number and widths of the gaps traversed by an x-ray or charged particle.

The overlapping portions described above in conjunction with FIGS. 4, 5 and 6 can be situated on adjacent surfaces of parallel leaves and/or on adjacent ends of opposing leaves as in the example of FIG. 2.

Figure 7:
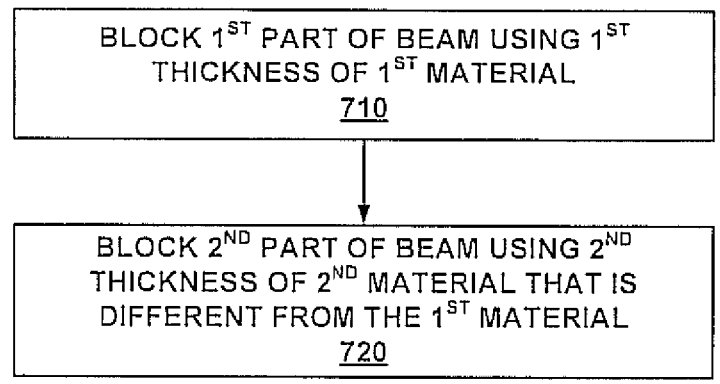
FIG. 7 is a flowchart of a method of shaping a beam of radiation according to an embodiment of the present invention.

FIG. 7 is a flowchart 700 of a method of shaping a beam of radiation according to an embodiment of the present invention. Although specific steps are disclosed in flowchart 700, such steps are exemplary. That is, the present invention is well-suited to performing various other steps or variations of the steps recited in flowchart 700.

In step 710, a first part of the beam is block (partially or completely, depending on the implementation) using a first thickness of a first material comprising a first portion of a first leaf in a multi-leaf collimator.

In step 720, a second part of the beam is blocked (partially or completely, depending on the implantation) using a second thickness of a second material comprising a second portion of the first leaf. The first portion extends from a surface of the second portion to prevent the first part of the beam from passing through a gap between the first leaf and a second leaf in the multi-leaf collimator. The second material is different from the first material and the first thickness is less than the second thickness.

In summary, according to embodiments of the present invention, the leaves of an MLC can be fabricated from a combination of materials. Specifically, a higher density/higher-Z material can be used in those portions of each leaf that overlap a corresponding portion of an adjacent leaf. The bulk of each leaf is made from a lower density/lower-Z material. Such leaves can be lighter, less expensive, easier to fabricate and will produce less neutrons or x-rays than conventional leaves made using only a high density or high-Z material, and thinner than conventional leaves made using only a low density or low-Z material.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments described herein were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A multi-leaf collimator for selectively blocking an incident beam of radiation, said collimator comprising:
   a plurality of independently adjustable leaves comprising a first leaf and a second leaf that is adjacent said first leaf, said first leaf having at least a first portion that extends from a substantially block-shaped second portion of said first leaf between said first leaf and said second leaf; wherein said first portion comprises a first material and said second portion comprises a second material that is different from said first material.

2. The collimator of claim 1 wherein said first portion is substantially block-shaped.

3. The collimator of claim 1 wherein said first portion has a cross-section that is substantially triangular in shape.

4. The collimator of claim 1 wherein said first material has a density that is greater than a density of said second material.

5. The collimator of claim 1 wherein an atomic number for said first material is greater than an atomic number for said second material.

6. The collimator of claim 1 wherein said first material is selected from the group consisting of: tungsten, tungsten alloys, tantalum, tantalum alloys, lead, and lead alloys; and wherein said second material is selected from the group consisting of: steel, brass, zinc, and copper.

7. The collimator of claim 1 wherein said first and second leaves are arranged side-by-side and are moveable in parallel.

8. The collimator of claim 1 wherein said first and second leaves are substantially aligned with each other and are moveable in opposite directions.

9. An apparatus comprising:
   a source operable for generating a beam of radiation onto a target area; and
   a multi-leaf collimator disposed between said source and said target area and operable for shielding said target area from said beam, wherein said collimator comprises at least a first pair of independently adjustable leaves that are moveable along a common line; said first pair of leaves including a first leaf having at least a first portion comprising a first thickness of a first material and a second portion comprising a second thickness of a second material that is different from said first material.

10. The apparatus of claim 9 wherein said second portion has a quadrilateral cross-section, wherein said cross-section is orthogonal to said common axis.

11. The apparatus of claim 9 wherein said first portion has a substantially quadrilateral cross-section, wherein said cross-section is orthogonal to said common axis.

12. The apparatus of claim 9 wherein said first portion has a substantially triangular cross-section, wherein said cross-section is orthogonal to said common axis.

13. The apparatus of claim 9 wherein said first thickness is less than said second thickness.

14. The apparatus of claim 9 wherein said first material is a higher density material and said second material is a lower density material.

15. The apparatus of claim 9 wherein said first material is a higher-Z material and said second material is a lower-Z material.

16. The apparatus of claim 9 wherein said first material is selected from the group consisting of: tungsten, tungsten alloys, tantalum, tantalum alloys, lead, and lead alloys; and wherein said second material is selected from the group consisting of: steel, brass, zinc, and copper.

17. The apparatus of claim 9 wherein said first pair of leaves comprises a second leaf separated from said first leaf by a gap, wherein said first material is disposed between said second material and said second leaf and wherein said first portion overlaps a corresponding portion of said second leaf.

18. The apparatus of claim 17 further comprising a second pair of independently adjustable leaves that are moveable along a common line, wherein said first and second pairs are arranged side-by-side and are moveable in parallel to each other.

19. A method of shaping an incident beam of radiation, said method comprising:
   blocking a first part of said beam using a first thickness of a first material comprising at least a first portion of a first leaf in a multi-leaf collimator; and
   blocking a second part of said beam using a second thickness of a second material comprising a second portion of said first leaf, said second portion having a substantially block shape, said second material different from said first material and said first thickness less than said second thickness, wherein said first portion extends from said second portion to prevent said first part of said beam from passing through a gap between said first leaf and a second leaf in said multi-leaf collimator.

20. The method of claim 19 wherein said first material has a density that is greater than a density of said second material.

21. The method of claim 19 wherein an atomic number for said first material is greater than an atomic number for said second material.

22. The method of claim 19 wherein said first material is selected from the group consisting of: tungsten, tungsten alloys, tantalum, tantalum alloys, lead, and lead alloys; and wherein said second material is selected from the group consisting of: steel, brass, zinc, and copper.

23. The method of claim 19 wherein said first and second leaves are arranged side-by-side and are moveable in parallel.

24. The method of claim 19 wherein said first and second leaves are substantially aligned with each other and are moveable in opposite directions.

25. The method of claim 19 wherein said first portion has a substantially rectilinear cross-section, wherein said cross-section is orthogonal to the longitudinal axis of said first portion.

\* \* \* \* \*